United States Patent [19]

Flynn et al.

[11] Patent Number: 5,484,783
[45] Date of Patent: Jan. 16, 1996

[54] HYPOCHOLESTEROLEMIC, ANTIATHEROSCLEROTIC AND HYPOTRIGLYCERIDEMIC MERCAPTOACETYLAMIDE AND BENZAZAPINE DERIVATIVES

[75] Inventors: Gary A. Flynn; John F. French; Richard C. Dage, all of Cincinnati, Ohio

[73] Assignee: Merrell Dow Pharmaceuticals Inc., Cincinnati, Ohio

[21] Appl. No.: 217,781

[22] Filed: Mar. 24, 1994

[51] Int. Cl.⁶ .......................... A61K 31/55; A61K 31/535
[52] U.S. Cl. .......................... 514/214; 540/521; 540/522
[58] Field of Search .......................... 514/214, 235

[56] References Cited

U.S. PATENT DOCUMENTS

| | | | |
|---|---|---|---|
| 3,334,091 | 7/1967 | Houlihan | 260/239.30 B |
| 3,334,095 | 8/1967 | Houluhan | 514/214 |
| 4,080,449 | 3/1978 | Croisier et al. | 514/214 |
| 4,320,057 | 3/1982 | Freed et al. | 260/239.30 B |
| 4,391,752 | 7/1983 | Crossley | 260/239.30 B |
| 4,399,136 | 8/1983 | Hassall et al. | 424/250 |
| 4,415,496 | 11/1983 | Harris et al. | 260/239.30 B |
| 4,487,929 | 12/1984 | Hassall et al. | 544/224 |
| 4,512,924 | 4/1985 | Attwood et al. | 260/243 |
| 4,584,294 | 4/1986 | Ruyle | 514/214 |
| 4,658,024 | 4/1987 | Attwood et al. | 540/500 |
| 4,692,438 | 9/1987 | Hassall et al. | 514/183 |
| 4,716,232 | 12/1987 | Ternansky | 548/112 |
| 4,734,504 | 3/1988 | Holmes | 548/364 |
| 4,734,505 | 3/1988 | Holmes | 548/364 |
| 4,762,924 | 8/1988 | Hassall et al. | 540/501 |
| 4,772,701 | 9/1988 | Attwood et al. | 544/235 |
| 4,782,149 | 11/1988 | Lawton et al. | 540/500 |
| 4,785,093 | 11/1988 | Hassall et al. | 540/460 |
| 4,808,713 | 2/1989 | Attwood et al. | 525/185 |
| 4,824,832 | 4/1989 | Flynn et al. | 514/214 |
| 4,826,980 | 5/1989 | Hassall et al. | 544/224 |
| 4,973,585 | 11/1990 | Flynn et al. | 514/214 |
| 5,208,230 | 5/1993 | Flynn et al. | 514/214 |
| 5,238,932 | 7/1994 | Flynn et al. | 514/214 |

FOREIGN PATENT DOCUMENTS

| | | |
|---|---|---|
| 0128728 | 12/1984 | European Pat. Off. . |
| 0249223 | 12/1987 | European Pat. Off. . |
| 0249224 | 12/1987 | European Pat. Off. . |
| 0322914 | 12/1988 | European Pat. Off. . |
| 0481522 | 4/1992 | European Pat. Off. . |
| 0492369 | 7/1992 | European Pat. Off. . |
| 0533084 | 3/1993 | European Pat. Off. . |
| 0599444 | 6/1994 | European Pat. Off. . |
| 9108195 | 6/1991 | WIPO . |
| 9109840 | 7/1991 | WIPO . |
| 9302099 | 2/1993 | WIPO . |

OTHER PUBLICATIONS

Davis, Harry R. et al., *Supplement I Circulation*, vol. 86, No. 4 p. I-220 (0873), (Oct. 1992).
Powell Jerry S. et al., *Journal of American College of Cardiology*, vol. 17, No. 6, pp. 137B–142B (May 1991).
Flynn, et al., J. Am. Chem. Soc. 109, 7914 (1987).
Flynn, et al., Peptide Chemistry (1987); T. Shiba & Sakakibara (ed.), Protein Research Foundation, Osaka (1988).
Flynn, et al., Tetrahedron Letters, vol. 31 (6), 815–88 (1990).
Attwood, et al., J. Chem. Soc. Perkin Trans. I, pp. 1011–1019 (1986).
Natoff, et al., Drugs of the Future, vol. 12 (5): 475–483 (1987).
J. Med. Chem. 1992, 35, 823–832, Timothy D. Ocain et al. Bioorganic and Medical Chem. Letters vo. 1, 309, 1991.
Fournie–Zaluski, Marie–Claude et al., *J. Med. Chem.*, 1992 vol. 35, pp. 2473–2481.
Fournie–Zaluski, Marie–Claude et al., *J. Med. Chem.*, 1992 vol. 35, pp. 1259–1266.
French, John F., *Jour. of Pharm and Exper. Therapeutics*, vol. 268, No. 1, pp. 180–186 1993.
W. H. Parsons et al. *Biochemical and Biophysical Research Communications* vol. 117, No. 1, 1993 (Nov. 30, 1983).
Kuglyama et al., *Circulation* "Abstract from the 66th Scientific Sessions" 88(4), 1993, p. I-521.
Burkholder, et al. *Bioorganic and Medical Chem. Letters*, vol. 3, No. 2, pp. 231–234, 1993.
Flynn et al., J. Med. Chem. 1993, 36 2420–2423.
Remington's Pharmaceutical Services (1980), 16th Edition, Mack Publishing Co. pp. 420–427.

*Primary Examiner*—T. J. Criares
*Attorney, Agent, or Firm*—Charlotte L. Barney

[57] ABSTRACT

The present invention relates to the use of certain mercaptoacetylamide and benzazapine derivatives in treating patients suffering from hypertriglyceridemia, atherosclerosis and hypercholesterolemia.

10 Claims, No Drawings

5,484,783

HYPOCHOLESTEROLEMIC, ANTIATHEROSCLEROTIC AND HYPOTRIGLYCERIDEMIC MERCAPTOACETYLAMIDE AND BENZAZAPINE DERIVATIVES

BACKGROUND OF THE INVENTION

Coronary heart disease (CHD) remains the leading cause of death in the industrialized countries. Despite recent declines in CHD mortality, CHD is still responsible for more than 500,000 deaths in the U.S. annually. It is estimated that CHD, directly and indirectly, costs the U.S. more than $100 billion a year. The primary cause of CHD is atherosclerosis, a disease characterized by the deposition of lipid (cholesterol and triglycerides) in the arterial vessel wall, resulting in a narrowing of the arterial lumen and ultimately hardening of the arteries.

Atherosclerosis as manifested in its major clinical complication, coronary heart disease (CHD) or ischaemic heart disease, continues to be a major cause of death in industrialized countries. It is now well accepted that atherosclerosis can begin with local injury to the arterial endothelium followed by the penetration of circulatory monocytes into the intima of the arterial wall where they become loaded with lipoprotein derived lipids. At about the same time there seems to be a migration of arterial smooth muscle cells from the medial layer to the intimal layer and their proliferation there along with the deposition of lipid and accumulation of foam cells in the lesion. As the atherosclerotic plaque develops it progressively occludes more and more of the affected blood vessel and can eventually lead to ischaemia, thrombosis or infarction. Therefore, it is desirable to provide methods of inhibiting the progression of atherosclerosis in patients in need thereof.

National Institutes of Health Consensus Development Conference Panel concluded that lowering plasma cholesterol levels (specifically blood levels of low-density lipoprotein cholesterol) will definitely reduce the risk of heart attacks due to CHD. Serum lipoproteins are the carriers for lipids in the circulation. They are classified according to their density; i.e., chylomicrons, very low-density lipoproteins (VLDL), intermediate density lipoproteins (IDL), low density lipoproteins (LDL) and high-density lipoproteins (HDL). About 50% to 70% of the cholesterol circulating in the blood is carried as LDL. In contrast, about 25% of total cholesterol is found in HDL, while VLDL carries most of the plasma triglycerides and only about 10% to 15% of the total cholesterol.

Chylomicrons are assembled in the intestinal wall from products of lipid digestion and are then transported into the peripheral circulation via the thoracicolymphatic system. In the circulation, they are broken down by lipoprotein lipase (LPL) into free fatty acids and triglycerides which are primarily used by muscles for energy or stored in adipose tissue. The other serum lipoproteins are involved in the transport of endogenously synthesized lipid. Endogenous lipid transport begins when the liver secretes triglycerides and cholesterol into the plasma as VLDL. The triglycerides of VLDL are cleaved in the capillaries by LPL to IDL and finally LDL. Some of these particles are cleared rapidly by the liver by receptor-mediated endocytosis. The remainder circulate mainly as LDL.

As cells die and cell membranes turn over, cholesterol is continuously released into the plasma and becomes HDL. HDL promotes the removal of cholesterol from peripheral cells and facilitates its transport back to the liver.

Arterial wall cholesterol is derived almost exclusively from LDL [Brown and Goldstein, Ann. Rev. Biochem. 52, 223 (1983); Miller, Ann. Rev. Med. 31, 97 (1980)]. Framingham investigators found the higher the levels of LDL, the higher the risk of devloping CHD [Am. J. Med. 80 (Suppl. 2A) 23–32, 1986]. In patients with low levels of LDL, the development of atheroschlerosis is rare [Patton et. al, Clin. Chem. 29, 1890 (1983)]. Accordingly, it is desirable to provide a method for reducing plasma cholesterol in patients with hypercholesterolemia or at risk of developing hypercholesterolemia.

Elevated cholesterol levels are also associated with a number of disease states, including coronary artery disease, angina pectoris, carotid artery disease, strokes, cerebral arteriosclerosis, and xanthoma. It is desirable to provide a method for reducing plasma cholesterol in patients with, or at risk of developing disease states associated with elevated cholesterol levels.

Hypertriglyceridemia is a condition in which there is an excessive amount of triglyceride (>500mg/dl) in the plasma. It may play a role in atherogenesis and the development of coronary heart disease [Vega and Grundy, Adv. Exp. Med. 243, 311 (1989)]. In addition, severe hypertriglyceridemia (>1000mg/dl) is associated with chylomicronemia and causes acute pancreatitis [See K. Soergel, ACUTE PANCREATITIS, in Gastrointestinal Disease 91, 3rd ed. (Sleisenger, M. H., and Fordtran, J. S., eds.), W. B. Saunders Company, Philadelphia, Pa., 1983, pp. 1462–1485; and See Brown, M. S., and Goldstein, J. L., DRUGS USED IN THE TREATMENT OF HYPERLIPOPROTEINEMIAS, in Goodman and Gillman's, The Pharmacological Basis of Therapeutics 34, 7th edition, (Macmillan Publishing Co., New York, 1985, pp. 827–845]. Severe elevations in chylomicrons directly induce pancreatitis, and it can be prevented by triglyceride reduction [U.S. Department of Health and Human Services, NIH Publication No. 89–2925, pp. 74–77, January 1989, "Report of the Expert Panel on Detection, Evaluation and Treatment of High Blood Cholesterol in Adults"] It is therefore desirable to provide a method for reducing plasma triglycerides in patients with hypertriglyceridemia.

The present invention relates to the use of certain mercaptoacetylamide derivatives known to be useful for the inhibition of Enkephalinase (EC 3.4.24.1) and ACE (EC 3.4.15.1) [Flynn, Warshawsky, Mehdi, Bey, Beight, Giroux and Burkholder, European Patent Application, Publication Number 0 481 522 A1, published Apr. 22, 1992] in treating patients suffering from hypercholesterolemia and atherosclerosis or hypertriglyceridemia.

SUMMARY OF THE INVENTION

The present invention provides a method of treating hypercholesterolemia, atheroscherosis and hypertriglyceridemia in a patient in need thereof comprising administering to said patient an effective hypocholesterolemic, antiatherosclerotic or hypotriglyceridemic amount of a compound of the Formula (I)

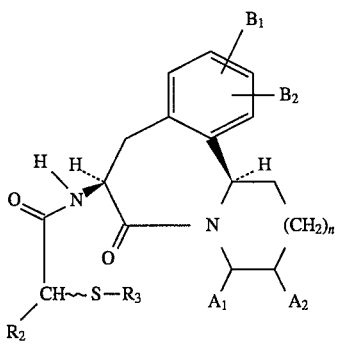

(I)

wherein

A₁ and A₂ are each independently hydrogen or —COOR₄ wherein R₄ is hydrogen; —CH₂O—C(O)C(CH₃)₃; a C₁-C₄ alkyl; an Ar—Y— group wherein Ar is aryl and Y is a C₀-C₄ alkyl; or diphenylmethyl; with the proviso that where A₁ is hydrogen, A₂ is —COOR₄, and where A₁ is —COOR₄, A₂ is hydrogen;

B₁ and B₂ are each independently hydrogen; hydroxy; —OR₅ wherein R₅ is a C₁-C₄ alkyl or an Ar—Y— group; or, where B₁ and B₂ are attached to adjacent carbon atoms, B₁ and B₂ can be taken together with said adjacent carbons to form a benzene ring or methylenedioxy;

R₂ is hydrogen, C₁-C₈ alkyl, —CH₂OCH₂CH₂OCH₃ or an Ar—Y— group;

R₃ is hydrogen, acetyl, —CH₂O—C(O)C(CH₃)₃ or benzoyl; and n is an integer 0 or 1.

The present invention further provides a method of treating hypercholesterolemia, atheroscherosis and hypertriglyceridemia in a patient in need thereof comprising administering to said patient an effective hypocholesterolemic, antiatherosclerotic or hypotriglyceridemic amount of a compound of the Formula (II) wherein

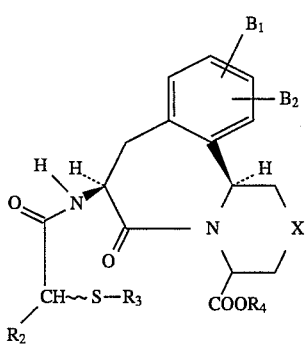

(II)

B₁ and B₂ are each independently hydrogen; hydroxy; —OR₅ wherein R₅ is a C₁-C₄ alkyl or an Ar—Y— group wherein Ar is aryl and Y is a C₀-C₄ alkyl; or, where B₁ and B₂ are attached to adjacent carbon atoms, B₁ and B₂ can be taken together with said adjacent carbons to form a benzene ring or methylenedioxy;

R₂ is hydrogen, C₁-C₈ alkyl, —CH₂OCH₂CH₂OCH₃ or an Ar—Y— group;

R₃ is hydrogen, acetyl, —CH₂O—C(O)C(CH₃)₃ or benzoyl;

R₄ is hydrogen, a C₁-C₄ alkyl or an Ar—Y— group, —CH₂O—C(O)C(CH₃)₃ or diphenylmethyl; and

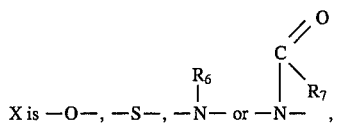

wherein R₆ is hydrogen, a C₁-C₄ alkyl or an Ar—Y— group and R₇ is —CF₃, C₁-C₁₀ alkyl or an Ar—Y— group.

DETAILED DESCRIPTION OF THE INVENTION

As used herein, the term "C₁-C₄ alkyl" refers to a saturated straight or branched chain hydrocarbyl radical of one to four carbon atoms and includes methyl, ethyl, propyl, isopropyl, n-butyl, isobutyl, tertiary butyl and the like. The terms "C₁-C₈ alkyl" and "C₁-C₁₀ alkyl" refer to saturated straight or branched chain hydrocarbyl radicals of one to eight and one to ten carbon atoms, respectively, including methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like.

As used herein, the term "Ar—Y—" refers to a radical wherein Ar is an aryl group and Y is a C₀-C₄ alkyl. The term "Ar" refers to a phenyl or naphthyl group unsubstituted or substituted with from one to three substituents selected from the group consisting of methylenedioxy, hydroxy, C₁-C₄ alkoxy, fluoro and chloro. The term "C₀-C₄ alkyl" refers to a saturated straight or branched chain hydrocarbyl radical of zero to four carbon atoms and includes a bond, methyl, ethyl, propyl, isopropyl, n-butyl, isobutyl, tertiary butyl and the like. Specifically included within the scope of the term "Ar—Y—" are phenyl, naphthyl, phenylmethyl or benzyl, phenylethyl, p-methoxybenzyl, 3,4-methylenedioxy, p-fluorobenzyl and p-chlorobenzyl.

As used herein, the designation "⁀⁀" refers to a bond to a chiral atom for which the stereochemistry is not designated.

As used herein, the term "patient" refers to warm-blooded animals or mammals, including rabbits, rodents, monkeys and humans, who are in need of treatment for hypertriglyceridemia atheroscherosis or hypercholesterolemia, such as, for example, in the case of a patient suffering from familial hyperlipidemia. Patients are in need of treatment for hypertriglyceridemia, for example, in the case of a patient suffering from Type IV Hyperlipoproteinemia (indicating elevated VLDL) according to the Fredrickson classification [Fredrickson and Levy, FAMILIAL HYPERLIPOPROTEINEMIA, in *The Metabolic Basis of Inherited Disease*, 3rd ed. (Stanbury, J. B.; Wyngaarden, J. B.; and Fredrickson, D. S.; eds.) McGraw-Hill Book Co., New York, 1972, pp. 545–614].

Hypercholesterolemia is a disease state characterized by levels of serum cholesterol or of LDL cholesterol which are elevated by a clinically significant amount over that considered normal by those of ordinary skill in the art. The identification of those patients who are in need of treatment for hypercholesterolemia is well within the ability and knowledge of one skilled in the art. For example, individuals who have serum cholesterol levels or LDL cholesterol levels, as determined by clinical laboratory tests, which are substantially and chronically elevated over that considered normal by those of ordinary skill in the art, are patients in need of treatment for hypercholesterolemia. By way of further example, individuals who are at risk of developing hypercholesterolemia can also be patients in need of treatment for hypercholesterolemia. A clinician skilled in the art can readily identify, by the use of clinical tests, physical examination and medical/family history, those patients who are suffering from hypercholesterolemia and those who are at risk of developing hypercholesterolemia and thus readily determine if an individual is a patient in need of treatment for hypercholesterolemia.

An effective hypocholesterolemic amount of a compound of Formula (I) or (II) is an amount which is effective in reducing serum cholesterol levels or LDL cholesterol levels in a patient in need thereof. As such, successful treatment of a patient for hypercholesterolemia is understood to include reducing a patient's serum cholesterol or LDL cholesterol levels. Successful treatment for hypercholesterolemia is also understood to include prophylaxis in preventing clinically significant elevations in serum cholesterol or in LDL cholesterol levels in a patient who is at risk of the development of hypercholesterolemia.

Atherosclerosis is a disease state characterized by the development and growth of atherosclerotic lesions or plaque. The identification of those patients who are in need of treatment for atherosclerosis is well within the ability and knowledge of one skilled in the art. For example, individuals who are either suffering from clinically significant atherosclerosis or who are at risk of developing clinically significant atherosclerosis are patients in need of treatment for atherosclerosis. A clinician skilled in the art can readily determine, by the use of clinical tests, physical examination and medical/family history, if an individual is a patient in need of treatment for atherosclerosis.

An effective antiatherosclerotic amount of a compound of Formula (I) or (II) is an amount which is effective in inhibiting development or growth of atherosclerosis in a patient in need thereof. As such, successful treatment of a patient for atherosclerosis is understood to include effectively slowing, interrupting, arresting, or stopping atherosclerotic lesion or plaque development or growth and does not necessarily indicate a total elimination of the atherosclerosis. It is further understood and appreciated by those skilled in the art that successful treatment for atherosclerosis can include prophylaxis in preventing atherosclerotic lesion or plaque formation.

An effective antiatherosclerotic or hypocholesterolemic dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective antiatherosclerotic or hypocholesterolemic amount of a compound of Formula (I) or (II) will generally vary from about 1 milligram per kilogram of body weight per day (mg/kg/day) to about 1000 milligrams per kilogram of body weight per day (1 gm/kg/day). A daily dose of from about 2 mg/kg to about 200 mg/kg is preferred.

In effecting treatment of a patient, a compound of Formula (I) or (II) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances.

Compounds of Formula (I) or (II) can be administered in the form of pharmaceutical compositions or medicaments which are made by combining the compound of Formula (I) or (II) with pharmaceutically acceptable carriers or excipients, the proportion and nature of which are determined by the chosen route of administration, and standard pharmaceutical practice.

Hypertriglyceridemia is a disease state characterized by levels of plasma triglycerides which are elevated by a clinically significant amount over that considered normal by those of ordinary skill in the art. The identification of those patients who are in need of treatment for hypertriglyceridemia is well within the ability and knowledge of one skilled in the art. For example, individuals who have plasma triglyceride levels, as determined by clinical laboratory tests, which are substantially and chronically elevated over that considered normal by those of ordinary skill in the art, are patients in need of treatment for hypertriglyceridemia. By way of further example, individuals who are at risk of developing hypertriglyceridemia can also represent patients in need of treatment for hypertriglyceridemia. A clinician skilled in the art can readily identify, by the use of clinical tests, physical examination and medical/family history, those patients who are suffering from hypertriglyceridemia and those who are at risk of developing hypertriglyceridemia and thus readily determine if an individual is a patient in need of treatment for hypertriglyceridemia.

An effective hypotriglyceridemic amount of a compound of Formula (1) or (II) is an amount which is effective in reducing plasma triglyceride levels in a patient in need thereof. As such, successful treatment of a patient for hypertriglyceridemia is understood to include reducing a patient's plasma triglyceride levels. Successful treatment for hypertriglyceridemia is also understood to include prophylaxis in preventing clinically significant elevations in plasma triglyceride levels in a patient who is at risk of the development of hypertriglyceridemia.

An effective hypotriglyceridemic dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective hypotriglyceridemic amount of a compound of Formula (1) or (II) will generally vary from about 1 milligram per kilogram of body weight per day (mg/kg/day) to about 1000 milligrams per kilogram of body weight per day (1.0 gm/kg/day). A daily dose of from about 1 mg/kg to about 200 mg/kg is preferred.

In effecting treatment of a patient, a compound of Formula (1) or (II) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances.

A compound of Formula (1) or (II) can be administered in the form of pharmaceutical compositions or medicaments which are made by combining a compound of Formula (1) or (II) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, a compound Formula (1) or (II) may be incorporated with excipients and used in the form of tablets, troches, capsules, elixirs, suspensions, syrups, wafers, chewing gums and the like. These preparations should contain at least 4% of the compound of formula (I) or (II), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, a compound of Formula (1) or (II) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

The compounds of Formula (I) and (II) can be prepared as described in European Patent Application, Publication Number 0 481 522 A1, published Apr. 22, 1992, hereby incorporated by reference.

The following example illustrates the utility of the mercaptoacetylamide derivatives of the present invention as hypocholesterolemic, antiatherosclerotic and hypocholesterolemic agents. This example is understood to be illustrative only and is not intended to limit the scope of the present invention in any way.

EXAMPLE 1

Rabbit Test for Hypocholesterolemic, Antiatherosclerotic and Hypotriglyceridemic Activities Feed rabbits a high cholesterol (1%) diet for eight weeks, supplementing the diets of certain rabbits with the agent of interest. At the end of eight weeks, sacrifice the rabbits, collect the serum and determine cholesterol and triglyceride levels by standard methods [*Hypertension* 15:327–331, 1990].

Dissect the aorta of each rabbit from the ascending arch to the iliac bifurcation, clean and prepare for staining with Sudan IV to determine areas of atherosclerotic lesion with the use of image analysis.

Make statistical comparisons between the control and drug-treated groups to determine the activity of the agent of interest.

What is claimed is:

1. A method of lowering total serum cholesterol in a patient in need thereof comprising administering to said patient a therapeutically effective hypocholesterolemic amount of a compound of the Formula

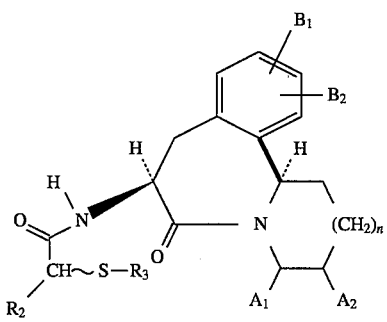

wherein $A_1$ and $A_2$ are each independently hydrogen or —$COOR_4$ wherein $R_4$ is hydrogen; —$CH_2O$—$C(O)C(CH_3)_3$; a $C_1$-$C_4$ alkyl; an Ar—Y— group wherein Ar is aryl and Y is a $C_0$-$C_4$ alkyl; or diphenylmethyl; with the proviso that where $A_1$ is hydrogen, $A_2$ is —$COOR_4$, and where $A_1$ is —$COOR_4$, $A_2$ is hydrogen;

$B_1$ and $B_2$ are each independently hydrogen; hydroxy; —$OR_5$ wherein $R_5$ is a $C_1$-$C_4$ alkyl or an Ar—Y— group; or, where $B_1$ and $B_2$ are attached to adjacent carbon atoms, $B_1$ and $B_2$ can be taken together with said adjacent carbons to form a benzene ring or methylenedioxy;

$R_2$ is hydrogen, $C_1$–$C_8$ alkyl, —$CH_2OCH_2CH_2OCH_3$ or an Ar—Y— group;

$R_3$ is hydrogen, acetyl, —$CH_2$—O—$C(O)C(CH_3)_3$ or benzoyl; and n is an integer 0 or 1.

2. A method of treating a patient for hypercholesterolemia comprising administering to said patient a therapeutically effective hypocholesterolemic amount of a compound of the Formula

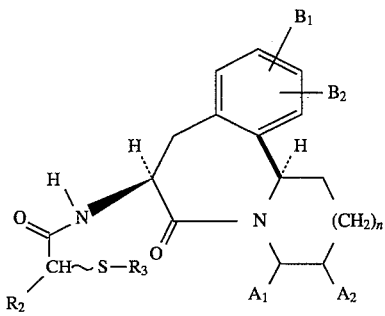

wherein $A_1$ and $A_2$ are each independently hydrogen or —$COOR_4$ wherein $R_4$ is hydrogen; —$CH_2O$—$C(O)C(CH_3)_3$; a $C_1$–$C_4$ alkyl; an Ar—Y— group wherein Ar is aryl and Y is a $C_0$–$C_4$ alkyl; or diphenylmethyl; with the proviso that where $A_1$ is hydrogen, $A_2$ is —$COOR_4$, and where $A_1$ is —$COOR_4$, $A_2$ is hydrogen;

$B_1$ and $B_2$ are each independently hydrogen; hydroxy; —$OR_5$ wherein $R_5$ is a $C_1$–$C_4$ alkyl or an Ar—Y— group; or, where $B_1$ and $B_2$ are attached to adjacent carbon atoms, $B_1$ and $B_2$ can be taken together with said adjacent carbons to form a benzene ring or methylenedioxy;

$R_2$ is hydrogen, $C_1$–$C_8$ alkyl, —$CH_2OCH_2CH_2OCH_3$ or an Ar—Y— group;

$R_3$ is hydrogen, acetyl, —$CH_2O$—$C(O)C(CH_3)_3$ or benzoyl; and n is an integer 0 or 1.

3. A method of lowering plasma triglycerides in a patient in need thereof comprising administering to said patient a therapeutically effective hypotriglyceridemic amount of a compound of the Formula

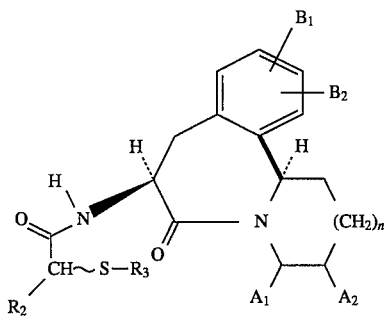

wherein $A_1$ and $A_2$ are each independently hydrogen or —$COOR_4$ wherein $R_4$ is hydrogen; —$CH_2O$—$C(O)C(CH_3)_3$; a $C_1$–$C_4$ alkyl; an Ar—Y— group wherein Ar is aryl and Y is a $C_0$–$C_4$ alkyl; or diphenylmethyl; with the proviso that where $A_1$ is hydrogen, $A_2$ is —$COOR_4$, and where $A_1$ is —$COOR_4$, $A_2$ is hydrogen;

$B_1$ and $B_2$ are each independently hydrogen; hydroxy; —$OR_5$ wherein $R_5$ is a $C_1$–$C_4$ alkyl or an Ar—Y— group; or, where $B_1$ and $B_2$ are attached to adjacent carbon atoms, $B_1$ and $B_2$ can be taken together with said adjacent carbons to form a benzene ring or methylenedioxy;

$R_2$ is hydrogen, $C_1$–$C_8$ alkyl, —$CH_2OCH_2CH_2OCH_3$ or an Ar—Y— group;

$R_3$ is hydrogen, acetyl, —$CH_2O$—$C(O)C(CH_3)_3$ or benzoyl; and n is an integer 0 or 1.

4. A method of treating a patient suffering from hypertriglyceridemia comprising administering to said patient a therapeutically effective hypotriglyceridemic amount of a compound of the Formula

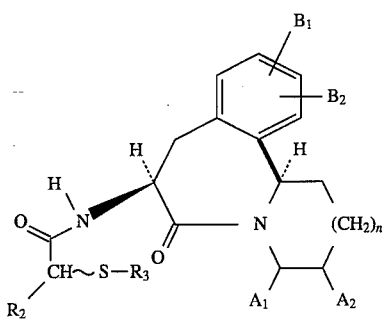

wherein $A_1$ and $A_2$ are each independently hydrogen or —$COOR_4$ wherein $R_4$ is hydrogen; —$CH_2O$—$C(O)C(CH_3)_3$; a $C_1$–$C_4$ alkyl; an Ar—Y— group wherein Ar is aryl and Y is a $C_0$–$C_4$ alkyl; or diphenylmethyl; with the proviso that where $A_1$ is hydrogen, $A_2$ is —$COOR_4$, and where $A_1$ is —$COOR_4$, $A_2$ is hydrogen;

$B_1$ and $B_2$ are each independently hydrogen; hydroxy; —$OR_5$ wherein $R_5$ is a $C_1$–$C_4$ alkyl or an Ar—Y— group; or, where $B_1$ and $B_2$ are attached to adjacent carbon atoms, $B_1$ and $B_2$ can be taken together with said adjacent carbons to form a benzene ring or methylenedioxy;

$R_2$ is hydrogen, $C_1$–$C_8$ alkyl, —$CH_2OCH_2CH_2OCH_3$ or an Ar—Y— group;

$R_3$ is hydrogen, acetyl, —$CH_2O$—$C(O)C(CH_3)_3$ or benzoyl; and n is an integer 0 or 1.

5. A method of lowering total serum cholesterol in a patient in need thereof comprising administering to said patient a therapeutically effective hypocholesterolemic amount of a compound of the Formula

11

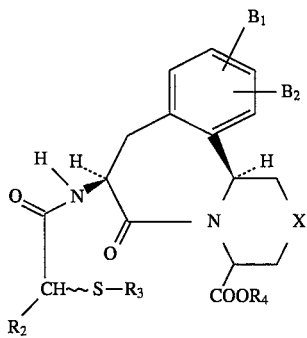

wherein $B_1$ and $B_2$ are each independently hydrogen; hydroxy; —$OR_5$ wherein $R_5$ is a $C_1$-$C_4$ alkyl or an Ar—Y— group wherein Ar is aryl and Y is a $C_0$-$C_4$ alkyl; or, where $B_1$ and $B_2$ are attached to adjacent carbon atoms, $B_1$ and $B_2$ can be taken together with said adjacent carbons to form a benzene ring or methylenedioxy;

$R_2$ is hydrogen, $C_1$-$C_8$ alkyl, —$CH_2OCH_2CH_2OCH_3$ or an Ar—Y— group;

$R_3$ is hydrogen, acetyl, —$CH_2O$—$C(O)C(CH_3)_3$ or benzoyl;

$R_4$ is hydrogen, a $C_1$-$C_4$ alkyl or an Ar—Y— group, —$CH_2O$—$C(O)C(CH_3)_3$ or diphenylmethyl; and

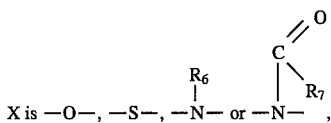

X is —O—, —S—, —N— or —N—, wherein $R_6$ is hydrogen, a $C_1$-$C_4$ alkyl or an Ar—Y— group and $R_7$ is —$CF_3$, a $C_1$-$C_{10}$ alkyl or an Ar—Y— group.

6. A method of treating a patient for hypercholesterolemia comprising administering to said patient a therapeutically effective hypocholesterolemic amount of a compound of the Formula

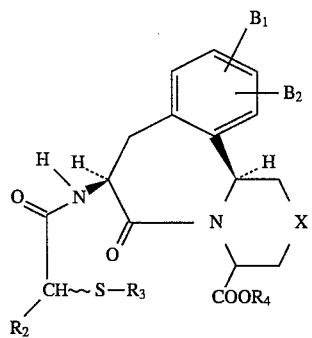

wherein $B_1$ and $B_2$ are each independently hydrogen; hydroxy; —$OR_5$ wherein $R_5$ is a $C_1$-$C_4$ alkyl or an Ar—Y— group wherein Ar is aryl and Y is a $C_0$-$C_4$ alkyl; or, where $B_1$ and $B_2$ are attached to adjacent carbon atoms, $B_1$ and $B_2$ can be taken together with said adjacent carbons to form a benzene ring or methylenedioxy;

$R_2$ is hydrogen, $C_1$-$C_8$ alkyl, —$CH_2OCH_2CH_2OCH_3$ or an Ar—Y— group;

12

$R_3$ is hydrogen, acetyl, —$CH_2O$—$C(O)C(CH_3)_3$ or benzoyl;

$R_4$ is hydrogen, a $C_1$-$C_4$ alkyl or an Ar—Y— group, —$CH_2O$—$C(O)C(CH_3)_3$ or diphenylmethyl; and

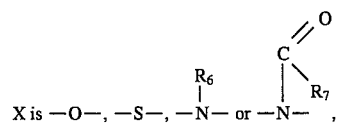

X is —O—, —S—, —N— or —N—, wherein $R_6$ is hydrogen, a $C_1$-$C_4$ alkyl or an Ar—Y— group and $R_7$ is —$CF_3$, a $C_1$-$C_{10}$ alkyl or an Ar—Y— group.

7. A method of lowering plasma triglycerides in a patient in need thereof comprising administering to said patient a therapeutically effective hypotriglyceridemic amount of a compound of the Formula

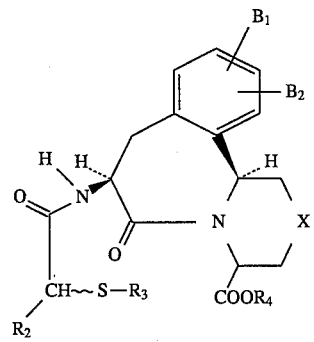

wherein $B_1$ and $B_2$ are each independently hydrogen; hydroxy; —$OR_5$ wherein $R_5$ is a $C_1$-$C_4$ alkyl or an Ar—Y— group wherein Ar is aryl and Y is a $C_0$-$C_4$ alkyl; or, where $B_1$ and $B_2$ are attached to adjacent carbon atoms, $B_1$ and $B_2$ can be taken together with said adjacent carbons to form a benzene ring or methylenedioxy;

$R_2$ is hydrogen, $C_1$-$C_8$ alkyl, —$CH_2OCH_2CH_2OCH_3$ or an Ar—Y— group;

$R_3$ is hydrogen, acetyl, —$CH_2O$—$C(O)C(CH_3)_3$ or benzoyl;

$R_4$ is hydrogen, a $C_1$-$C_4$ alkyl or an Ar—Y— group, —$CH_2O$—$C(O)C(CH_3)_3$ or diphenylmethyl; and

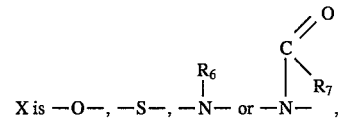

X is —O—, —S—, —N— or —N—, wherein $R_6$ is hydrogen, a $C_1$-$C_4$ alkyl or an Ar—Y— group and $R_7$ is —$CF_3$, a $C_1$-$C_{10}$ alkyl or an Ar—Y— group.

8. A method of treating a patient suffering from hypertriglyceridemia comprising administering to said patient a therapeutically effective hypotriglyceridemic amount of a compound of the Formula

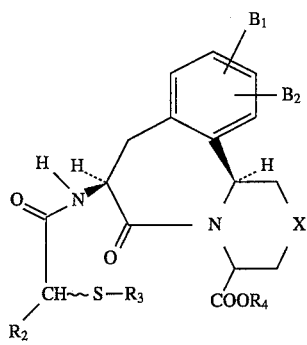

wherein

B₁ and B₂ are each independently hydrogen; hydroxy; —OR₅ wherein R₅ is a $C_1$–$C_4$ alkyl or an Ar—Y— group wherein Ar is aryl and Y is a $C_0$–$C_4$ alkyl; or, where B₁ and B₂ are attached to adjacent carbon atoms, B₁ and B₂ can be taken together with said adjacent carbons to form a benzene ring or methylenedioxy;

R₂ is hydrogen, $C_1$–$C_8$ alkyl, —CH₂OCH₂CH₂OCH₃ or an Ar—Y— group;

R₃ is hydrogen, acetyl, —CH₂O—C(O)C(CH₃)₃ or benzoyl;

R₄ is hydrogen, a $C_1$–$C_4$ alkyl or an Ar—Y— group, —CH₂O—C(O)C(CH₃)₃ or diphenylmethyl; and

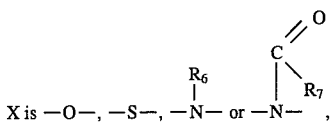

wherein R₆ is hydrogen, a $C_1$–$C_4$ alkyl or an Ar—Y— group and R₇ is —CF₃, a $C_1$–$C_{10}$ alkyl or an Ar—Y— group.

9. A method according to any of claims 1–8 wherein the compound is [4S-[4α, 7α(R*), 12bβ]]-7-[(1-oxo-2(S)-acetylthio- 3-phenylpropyl)amino]-1,2,3,4,6,7,8,12b-octahydro-6-oxo-pyrido[2,1-a][2]benzazepine- 4-carboxylic acid.

10. A method according to any of claims 1–8 wherein the compound is [4S-[4α, 7α(R*), 12bβ]]-7-[ (1-oxo-2(S)-thio-3-phenylpropyl)amino]-1,2,3,4,6,7,8,12b-octahydro-6-oxopyrido[ 2,1-a][2]benzazepine-4-carboxylic acid.

* * * * *